May 10, 1932. L. BURBANK Plant Pat. 16
PLUM
Filed Sept. 23, 1930
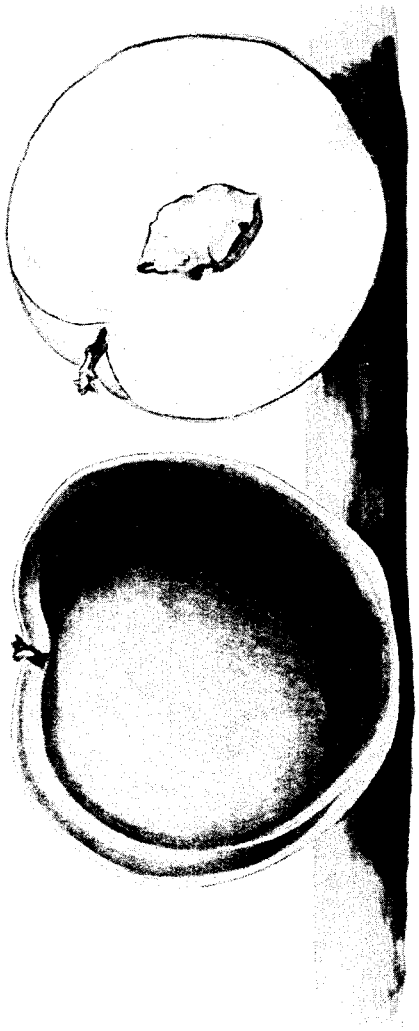
E. W. BURBANK
Executrix of
LUTHER BURBANK, Deceased.
By Robert Cobb
Attorneys Patented May 10, 1932

Plant Pat. 16

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S. NURSERIES & ORCHARDS COMPANY, OF LOUISIANA, MISSOURI

PLUM

Application filed September 23, 1930. Serial No. 483,937.

This invention relates to a new and distinct variety of plum.

This new variety is an early ripening, red skinned, golden fleshed plum very large in size. Because of its surpassing firmness and thick, tough skin, it is an exceptionally good shipper. It is striking in appearance not only because of its great size and shape but due also to its appealing colorful beauty. The general appearance, skin structure and firmness, give the plum the desirable quality necessary for a plum that must be shipped long distances and still retain its firmness and beauty.

The annexed drawings and following specification point out the prominent distinctions and characteristics of the new variety of plum which has been asexually reproduced.

*Young trees in nursery row*

*Tree.*—The tree's growth is moderately vigorous. The tree's branching habit is shapely divergent with acute forks. The bark on the new growth is Dresden brown, completely covering the courge green undercolor of the younger twigs, which are completely overspread with ocher red on the exposed side.

*Twigs.*—The twigs are medium to slender, and have short internodes. The bark is smooth, rather dull, modified by numerous light brown longitudinal cracks, becoming more prominent on older growth. The dormant buds are small, blunt, brown, and appressed.

*Foliage.*—The leaf on normal new growth is medium to small; the blade is about 3 inches long and 1⅜ inches wide. The sides are regular or slightly wavy, somewhat folded. The base is acute; apex nearly acuminate. The texture is rather thick and leathery. The margin is double crenate. Each projection of the margin is tipped with two or three minute reddish brown glands. The upper surface is somewhat glossy, with wrinkled appearance because of the depressed midrib and numerous veins. The color is Varley's green. The lower surface is smooth, modified by the prominent pink-tinged midrib and light green veins. The color is light elm green (approximate) as affected by the surface layer of white cells. There is only a trace of pubescence.

*Petiole.*—The petiole is rather stout in proportion to size of leaf. The upper side is grooved and roughened by numerous glands. The under side is smooth, tinged pink.

*Glands.*—There are from six to ten glands, often irregularly placed; their shape is globlose and they are reddish in color, becoming flattened and dark brown with maturity or through injury.

*Fruit*

*Form.*—The shape of the plum is cordate with a tendency to round-cordate. It is somewhat variable and irregular in form, having unequal sides. The size is very large, being about 2⅜ inches shortest transverse diameter. The base is rather narrow and has a very short, stout stem, ⅜ to ½ inch in length. The cavity is deep, medium wide, acuminate, accentuating the "short stemmed" appearance. The suture is deep and wide beginning in the cavity and extending to the apex. The apex is flattened and oblique on account of the protuberance giving the cordate form.

*Color.*—The color of the surface is a pale orange-yellow, almost entirely overspread with light coral red shading to pomegranate purple. Numerous dots are intermingled on the surface, some areolar with white point, some russet and conspicuous, considerably modifying the color effect.

*Skin.*—The skin is thick, tough and very waxy.

*Stone.*—The stone or seed is irregular oval to ovate and variable in several characters; is of medium size to rather large measuring about 1 inch long, ¾ of an inch wide and about ⅜ inch thick. The ventral suture is usually sharply winged, often irregular flanked by irregular or broken furrow. The dorsal suture is usually a rough ridge sometimes furrowed and attended by peculiar depressions or pockets. The sides are pitted and with prominent ridges near stem end. The color is pale yellow orange or orange buff when freed from the adhering flesh, and dry. The stone is a semi-cling to clingstone.

*Flesh.*—The flesh is fairly firm in shipping stage, becoming tender and very juicy when mature. It is slightly stringy, and fine grained for a large plum, the flavor being mild to sweet aromatic, and of excellent quality. The flesh in color is a pale orange yellow and translucent. (The above colors are in accordance with Ridgeway's Color Standard.)

It is to be understood that the foregoing characteristics are typical but subject perhaps to slight variation which may arise by reason of change of environment.

I claim:

The plum tree herein described characterized by the shape and color of its fruit and the size of its seed, as shown.

In testimony whereof I affix my signature.

ELIZABETH WATERS BURBANK,
*Known also as Elizabeth Burbank, Executrix of Luther Burbank, Deceased.*